Figure 1:
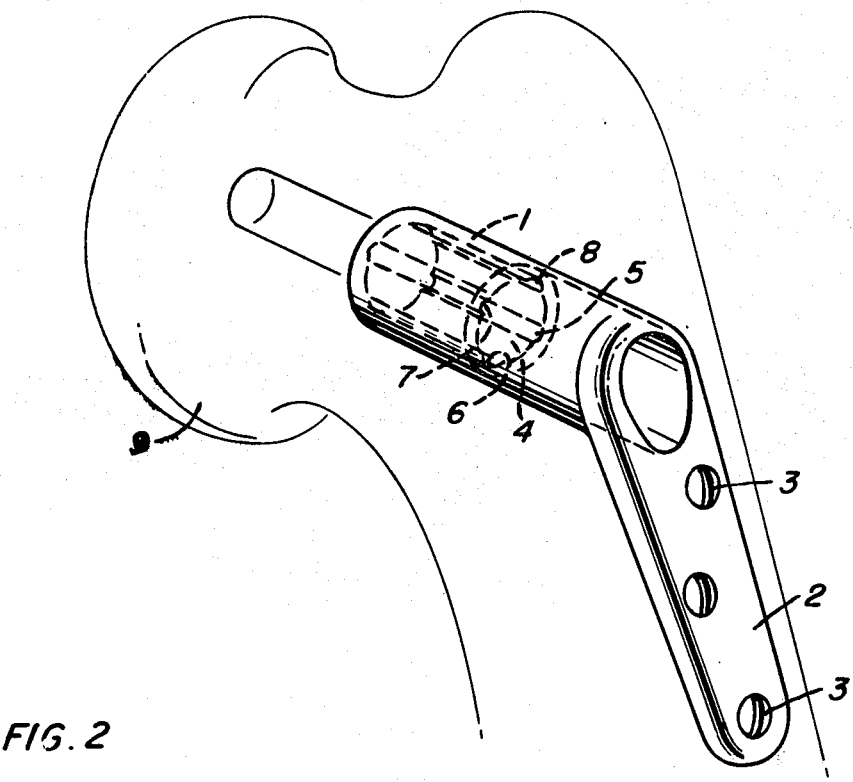

United States Patent [19]

Rydell et al.

[11] 4,441,492

[45] Apr. 10, 1984

[54] AID FOR TELESCOPIC NAIL FOR ORTHOPEDIC USE

[76] Inventors: Nils Rydell, Stenhammarsvägen 25, 161 52 Bromma; Ragnar Kalén, Golfvägen 26, 181 31 Danderyd, both of Sweden

[21] Appl. No.: 468,967

[22] Filed: Feb. 23, 1983

[30] Foreign Application Priority Data

Sep. 29, 1982 [SE] Sweden ................... 8205544

[51] Int. Cl.³ .................................... A61F 5/04
[52] U.S. Cl. .................... 128/92 EB; 128/92 CA; 128/92 BA
[58] Field of Search ......... 128/92 EB, 92 BA, 92 BB; 408/241 G

[56] References Cited

U.S. PATENT DOCUMENTS

| 2,200,120 | 5/1940 | Nauth ........................ 128/92 EB |
| 2,725,053 | 11/1955 | Bambara et al. ............... 128/92 EB |
| 3,002,514 | 10/1961 | Deyerle ....................... 128/92 EB |
| 4,095,591 | 6/1978 | Graham, Jr. et al. ........... 128/92 EB |

Primary Examiner—Richard J. Apley
Assistant Examiner—D. J. Isabella
Attorney, Agent, or Firm—Dennison, Meserole, Pollack & Scheiner

[57] ABSTRACT

An auxiliary tool used with an orthopedic compression system having a hollow barrel member coacting with nail means, the tool comprising an elongated rod engageable within the barrel member and having at least one longitudinal groove on its exterior surface which aligns and cooperates with a similar groove on the interior surface of the barrel to form an essentially cylindrical channel for guidance of drill means used to form an internal groove within the bone which is to receive the nail.

10 Claims, 5 Drawing Figures

AID FOR TELESCOPIC NAIL FOR ORTHOPEDIC USE

The present invention relates to an aid for telescopic nails. A telescopic nail has been found practical in correctly setting fragments in the case of broken bones. The fracture is secured by drilling a hole from the outer surface of one fragment, the hole passing substantially centrally through both fragments. A telescopic nail is then inserted in the hole, its outer end being adjustable by means of an adjustment means to regulate the depth of the telescopic nail. From its outer end the telescopic nail is provided with a hole which does not run through the length of the nail but at the front is in communication with a transverse hole. A pin is inserted in the axial hole of the telescopic nail, its front end passing the transverse hole in the telescopic nail and thereby being bent to hook shape. The pin is anchored in the free end of the telescopic nail. When this has been done the telescopic nail is adjusted so that the two fragments are brought into intimate and correct contact with each other. Such a telescopic nail generally has circular cross-section and is provided with longitudinal ridges to prevent the nail from turning about its own longitudinal axis. According to a further development of the telescopic nail, aimed at even more reliably preventing the nail from turning about its own axis, a telescope sleeve has been developed, provided with an outwardly directed flange. The telescope sleeve has an inner diameter substantially corresponding to the outer diameter of the telescopic nail. The telescope sleeve is also provided on its inner surface with grooves cooperating with the ridges of the telescopic nail. When setting a fracture, a hole is drilled in one fragment for the sleeve, the sleeve being secured to this fragment's outer surface by means of said flange, the flange abutting against the fragment and having holes for screws. When the sleeve is applied a hole is made for the telescopic nail itself. Thereafter the telescopic nail is inserted in the sleeve and the telescopic nail passes through the inner end of the sleeve. In front of the inner end is a circular hole. There are no grooves for the ridges in the telescopic nail; these will be punched out. The development described makes it impossible for the telescopic nail to turn about its axis. However, it has been found a distinct disadvantage that the grooves for the ridges inside the fragment must be punched out. The object of the present invention is to avoid the drawback of having to punch out the grooves for the telescopic nail ridges. According to the invention the ridges can be produced by drilling, in the same way as the central hole in the two fragments is produced. To enable the internal grooves to be produced in the two fragments by drilling, a drill guide is required. This consists of an elongate body provided with longitudinal grooves. The body has an outer diameter corresponding to the inner diameter of the sleeve. Together with a groove on the inner surface of the sleeve each groove in the elongate body forms a circular guide hole for a drill. A drill can thus be inserted in such a groove and acquire fully satisfactory guiding. When the drill passes the front end of the sleeve it will produce an internal groove in the fragment without the necessity of punching.

The elongate body is provided at its external end with a head having through-holes, each hole forming the start of the elongate external grooves. The elongate body is provided with adjustment members to enable setting of the depth of penetration of the body to the desired value. This setting is preferably achieved by providing the body with a number of holes arranged one after the other, through which a transverse unit is inserted in such a way that a part of it protrudes from the body. The unit may consist of a screw, in which case the corresponding hole must be threaded.

Usually each telescopic nail is provided with four ridges arranged symmetrically and the elongate body should therefore be provided with four external grooves.

According to an alternative the elongate body may be provided with only three grooves. A circular locking rod is then inserted into one of the grooves to secure the elongate body. When inserted into said sleeve, the elongate body will then be secured by the locking rod. It is thus possible to produce two grooves in the bone fractures. To produce the other two grooves, the elongate body is withdrawn and the body turned so that the other two grooves can be drilled in the fractures when the elongate body is again inserted into the sleeve.

It is no doubt obvious that a telescopic nail may be provided with a greater or smaller number of ridges and in that case the number of grooves in the drill guide must be the same.

Further characteristics of the present invention are revealed in the following claims.

Figure 2:
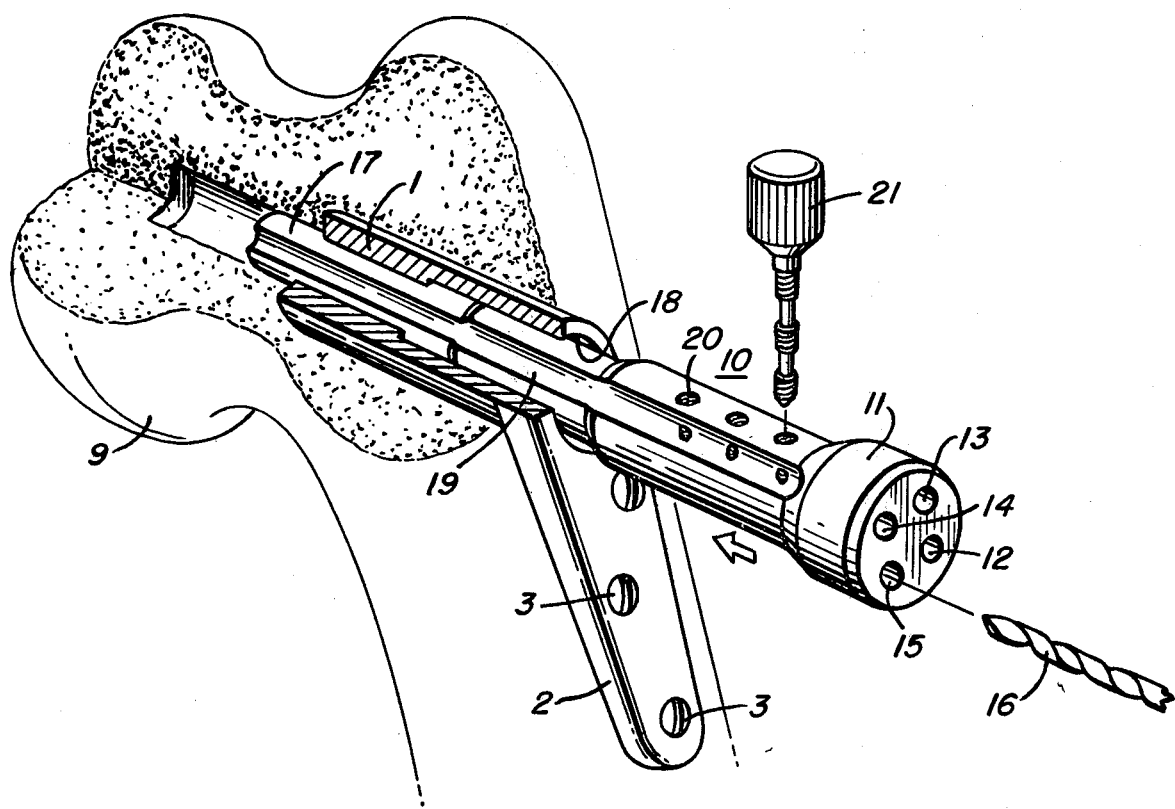
Figure 3:
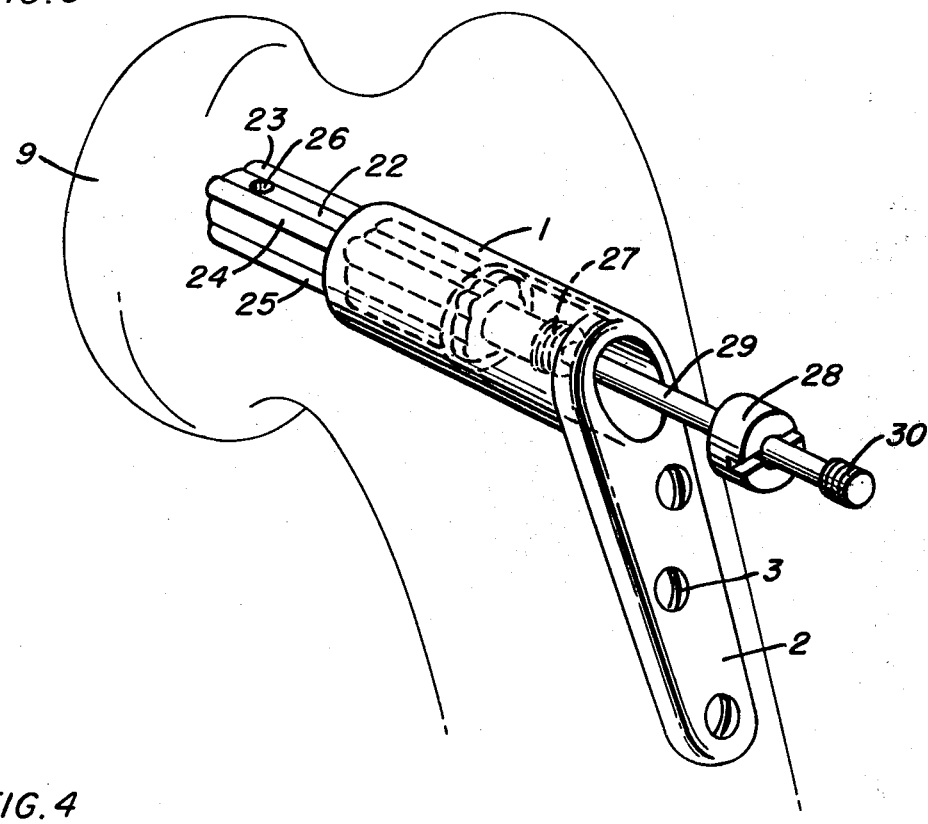
Figure 4:
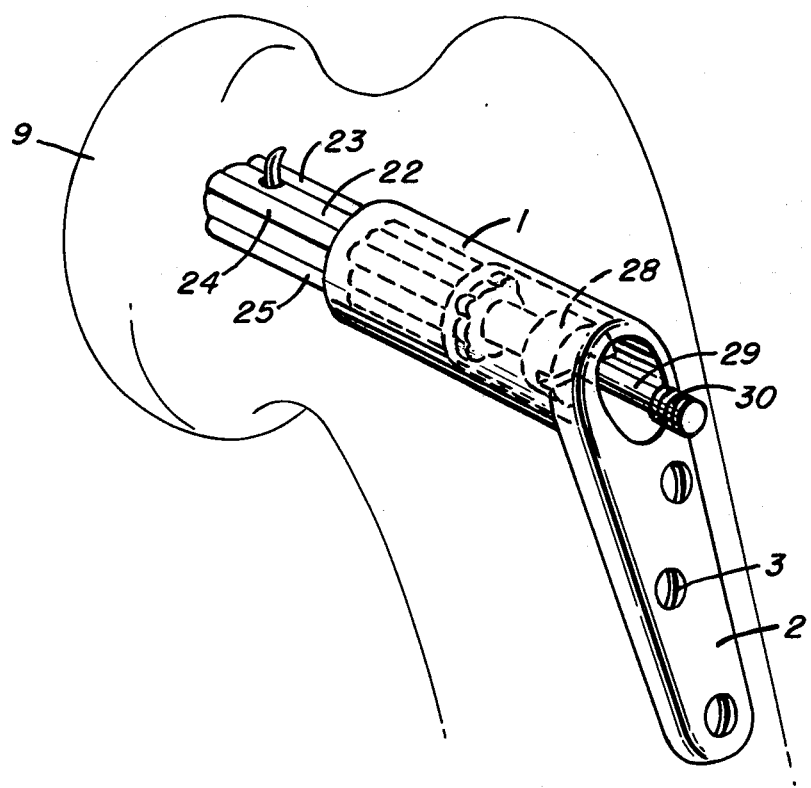
Figure 5:
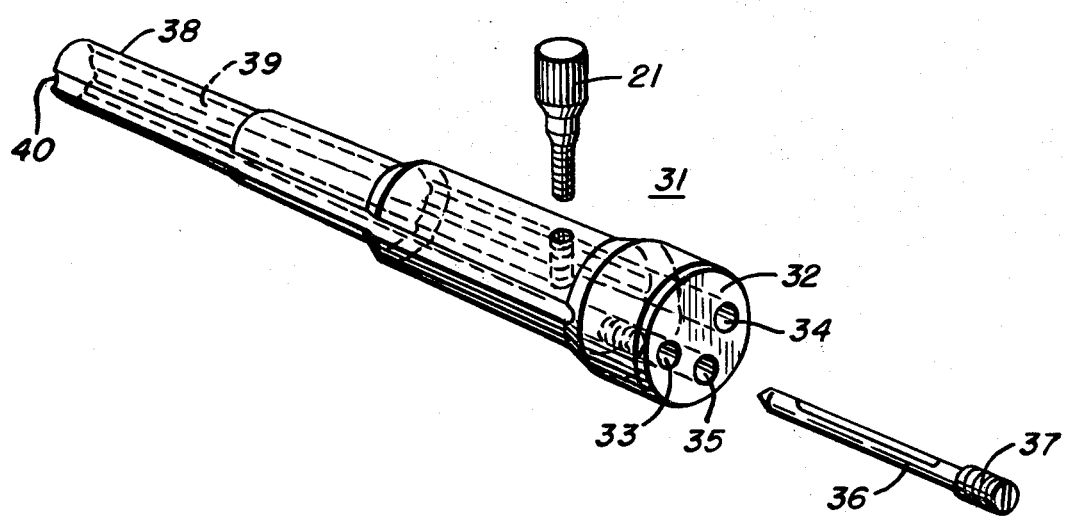

The invention will be described more fully with reference to the accompanying five sheets of drawings, in which FIG. 1 shows the upper part of a thigh-bone provided with a telescope sleeve with anchoring flange for a telescopic nail, FIG. 2 shows the telescope sleeve according to FIG. 1 in cooperation with a drill guide, FIG. 3 shows the telescopic sleeve according to FIG. 1 provided with telescopic nail and a pin, FIG. 4 shows telescopic nail and pin placed in position to hold together a fracture, and FIG. 5 shows a second embodiment of a drill guide.

The drawings show the neck of a femur 9 with a hole for a telescope sleeve or hollow barrel member 1. The sleeve is provided with an anchoring flange 2 in contact with the thigh-bone. The flange 2 is screwed into the thigh-bone by screws 3. A greater or fewer number of screws may of course be used. The telescope sleeve is thus anchored so that it cannot be turned. The sleeve or hollow barrel member 1 and the anchoring flange 2 define a compression plate means. In front of the telescope sleeve 1 is a hole for a telescope nail, to be described later. The telescope sleeve has a circular hole 4 provided with four symmetrically arranged grooves 5–8. This hole is so arranged that a contact surface is arranged where said grooves 5–8 start. A continuation of the grooves 5–8 is necessary in a hole in the thigh-bone, arranged in front of the grooves 5–8. For this purpose a drill guide 10 is inserted in the hole 4. The drill guide is provided at its righthand end with a cylindrical head 11, provided with four axially arranged through-running guide holes 12–15 for a drill 16. In front of the head 11 the drill guide is provided with a cylindrical rod 17 provided with grooves having an external diameter corresponding to the internal diameter of the hole 4. The rod 17 is provided with four axial grooves, two of which are visible, i.e. grooves 18 and 19. The surface of the grooves is of cylindrical nature and each groove constitutes a continuation of the holes 12–15. The four grooves 18–19 are arranged to cooperate with the grooves 5–8 in the hole 4. The cooperating grooves form circular holes or channels which are a continuation of the holes 12–15. The drill guide is provided with a number of transverse holes 20. A locking screw or pin 21 can be inserted into said holes. The locking screw or pin 21 limits the depth to which the drill guide 10 can be inserted. The locking screw is thus in abutment with the anchoring flange 2.

When the drill guide 10 has reached the desired depth, the drill 16 is inserted into each of the holes 12–15 in turn, producing four drilled grooves in the thigh-bone in front of the telescope sleeve 1. When drilling is finished a telescopic nail 22 with four ridges cooperating with the grooves 5–8 in the telescope sleeve 1 can be inserted into the telescope sleeve and into the hole before it in the thigh-bone. The visible ridges on the telescopic nail 22 are designated 23–25. The telescopic nail 22 has a hole leading from its righthand end and finishing in a transverse hole 26. The telescopic nail 22 is provided at its righthand end with a thread 27 cooperating with a nut 28. When the nut 28 is screwed on to the thread 27 and the telescopic nail 22 is inserted in the desired position, the nut 28 shall be screwed to abutment with the contact surface of the hole 4. A pin 29 is inserted so far into the righthand end of the telescopic nail 22 that its front end is bent to the shape shown in FIG. 4. The pin 29 is provided at its righthand end with a thread 30 to cooperate with a tool facilitating insertion and removal of the pin 29. The pin 29 is brought into abutment with the nut 28. Actuation of the nut 28 once it is in abutment with the contact surface of the hole 4 brings the two fractures into intimate contact with each other and into the correct position.

FIG. 5 shows an alternative drill guide in accordance with FIG. 2. The drill guide of FIG. 5 differs from that of FIG. 2 in that only two holes with following guide grooves are used for making the four grooves in the thigh-bone hole in front of the telescope sleeve 1. The head 32 of the drill guide 31 thus has three through-holes 33–35. The drill guide also has a locking screw 21 and hole cooperating therewith. A guide rod 38 is arranged before the head 32, corresponding to the guide rod 17 in FIG. 2. The guide rod 38 is provided with grooves 39 and 40 which cooperate with the holes 33 and 34. The hole 35 also cooperates with a groove on the rod 38 but has limited extension, corresponding approximately to the length of a groove in the telescope sleeve 1. A locking rod or pin 36 cooperates with the hole 35, the rod 36 being provided with a thread 37 cooperating with a thread inside the hole 35. When a drill guide 31 is inserted in the hole 4 of the telescope sleeve 1 the drill guide will be immediately positioned thanks to the locking rod 36. Two grooves can now be made in the hole in front of the telescope sleeve. The other grooves are made by withdrawing the groove guide 31 from the telescope sleeve 1 and turning it so that the holes 33 and 34 assume a position allowing the two remaining holes to be made in the hole in front of the telescope sleeve 1.

We claim:

1. Auxiliary tool to be used with a telescopic compression system for orthopedic application, said telescopic system comprising a compression plate means having a hollow barrel member provided with means for coacting with a nail means to nonrotatably join said plate means and a bone fragment located on a side opposite the plate means across the fractured site, wherein said barrel member being provided on its inner surface with at least one longitudinal groove extending the length thereof to cooperate with a complementary longitudinal ridge formed on the exterior surface of said nail means;

said tool comprising an elongate rod designed to fit within said barrel member and said rod having at least one longitudinal groove formed on its exterior surface such that when the tool is properly aligned with the longitudinal groove of said barrel means, the two coacting grooves form an essentially cylindrical channel thereby providing guidance for a drill means along the length of said channel.

2. The auxiliary tool of claim 1 wherein said elongate rod is provided with an enlarged head on one end thereof, said head having at least one axial hole defined therethrough and aligning with said at least one longitudinal groove for the guiding introduction of the drill means along the length of said channel.

3. The auxiliary tool of claim 2 wherein the elongate rod includes means regulating the depth of penetration of the elongate rod into the hollow barrel member.

4. The auxiliary tool of claim 3 wherein said means regulating the depth of penetration of the elongate rod includes a number of consecutive transverse holes along the length of the rod inward of the enlarged head, and a pin received in any selected one of said transverse holes.

5. The auxiliary tool of claim 4 wherein the barrel member is provided on its inner surface with multiple grooves extending along the length thereof, said rod having multiple grooves aligned with the barrel grooves to form multiple channels.

6. The auxiliary tool of claim 5 including a locking pin receivable in one of the channels formed by the grooves of the rod and the grooves of the hollow barrel member.

7. The auxiliary tool of claim 1 wherein the elongate rod includes means regulating the depth of penetration of the elongate rod into the hollow barrel member.

8. The auxiliary tool of claim 7 wherein said means regulating the depth of penetration of the elongate rod includes a number of consecutive transverse holes along the length of the rod inward of the enlarged head, and a pin received in any selected one of said transverse holes.

9. The auxiliary tool of claim 1 wherein the barrel member is provided on its inner surface with multiple grooves extending along the length thereof, said rod having multiple grooves aligned with the barrel grooves to form multiple channels.

10. The auxiliary tool of claim 9 including a locking pin receivable in one of the channels formed by the grooves of the rod and the grooves of the hollow barrel member.

* * * * *